(12) United States Patent
Le Goff et al.

(10) Patent No.: US 11,769,894 B2
(45) Date of Patent: Sep. 26, 2023

(54) BIOCELL WITH FUEL RESERVOIR

(71) Applicants: CENTRE NATIONAL DE LA RECHERCHE SCIENTIFIQUE, Paris (FR); UNIVERSITÉ GRENOBLE ALPES, Saint-Martin-d'Heres (FR); ECOLE CENTRALE DE LYON, Ecully (FR); UNIVERSITÉ CLAUDE BERNARD LYON 1, Villeurbanne (FR)

(72) Inventors: Alan Le Goff, Crêts-en-Belledonne (FR); Yannig Nedellec, Grenoble (FR); Caroline Abreu, Sens (FR); Serge Cosnier, Crolles (FR); Michaël Holzinger, Saint-Laurent-du-Pont (FR)

(73) Assignees: CENTRE NATIONAL DE LA RECHERCHE SCIENTIFIQUE, Paris (FR); UNIVERSITÉ GRENOBLE ALPES, Saint-Martin-d'hères (FR); ECOLE CENTRALE DE LYON, Ecully (FR); UNIVERSITÉ CLAUDE BERNARD LYON 1, Villeurbanne (FR)

( * ) Notice: Subject to any disclaimer, the term of this patent is extended or adjusted under 35 U.S.C. 154(b) by 470 days.

(21) Appl. No.: 16/972,928

(22) PCT Filed: May 31, 2019

(86) PCT No.: PCT/IB2019/054544
§ 371 (c)(1),
(2) Date: Dec. 7, 2020

(87) PCT Pub. No.: WO2019/234573
PCT Pub. Date: Dec. 12, 2019

(65) Prior Publication Data
US 2021/0249676 A1    Aug. 12, 2021
US 2022/0123342 A9    Apr. 21, 2022

(30) Foreign Application Priority Data

Jun. 8, 2018 (FR) ..................... 18/55014

(51) Int. Cl.
*H01M 8/16* (2006.01)
*H01M 50/491* (2021.01)
(Continued)

(52) U.S. Cl.
CPC .............. *H01M 8/16* (2013.01); *C12N 9/001* (2013.01); *C12N 9/0006* (2013.01);
(Continued)

(58) Field of Classification Search
CPC ...................................................... H01M 8/16
See application file for complete search history.

(56) References Cited

U.S. PATENT DOCUMENTS

| 8,642,308 B1 * | 2/2014 | Atanassov ........... C12N 9/0057 435/181 |
| 2013/0280509 A1 | 10/2013 | Alvarado Chacon et al. |
| 2015/0280266 A1 | 10/2015 | Nakagawa et al. |

OTHER PUBLICATIONS

Koessler, Jean-Luc; International Search Report; PCT/IB2019/054544; dated Sep. 23, 2019; 4 pages.
(Continued)

*Primary Examiner* — Amanda C. Walke
(74) *Attorney, Agent, or Firm* — Bradley Arant Boult Cummings LLP (57) ABSTRACT

The invention relates to a biocell (1) with a biofuel reservoir intended to be brought into contact with a liquid medium and with a fluid medium comprising an oxidant. Said biocell comprises a first electrochemical cell having: an anode (5) comprising a first enzyme capable of catalyzing the oxidation of the biofuel; —a cathode (7) comprising a second enzyme capable of catalyzing the reduction of the oxidant; and —a separating and porous membrane (3), electrically
(Continued)

insulating, and permeable to said liquid medium, placed between the anode (5) and the cathode (7). Said biocell (1) being characterized in that it comprises a means for storing the biofuel (3) and for providing the liquid medium to the anode (5), said means comprising a hydrophilic porous material in contact with said anode (5)) and having a basis weight of 500 to 900 g/m2.

12 Claims, 6 Drawing Sheets

(51) Int. Cl.
| | | |
|---|---|---|
| | *C12N 9/04* | (2006.01) |
| | *C12N 9/02* | (2006.01) |
| | *H01M 4/86* | (2006.01) |
| | *H01M 4/96* | (2006.01) |
| | *H01M 8/04186* | (2016.01) |
| | *H01M 8/04082* | (2016.01) |
| | *H01M 8/04858* | (2016.01) |
| | *B82Y 30/00* | (2011.01) |
| | *B82Y 40/00* | (2011.01) |

(52) U.S. Cl.
CPC ........... *H01M 4/8657* (2013.01); *H01M 4/96* (2013.01); *H01M 8/04186* (2013.01); *H01M 8/04216* (2013.01); *H01M 8/04902* (2013.01); *H01M 50/491* (2021.01); *B82Y 30/00* (2013.01); *B82Y 40/00* (2013.01); *C12Y 101/03004* (2013.01); *C12Y 101/05* (2013.01); *C12Y 103/03005* (2013.01)

(56) References Cited

OTHER PUBLICATIONS

Abreu, Caroline, et al.; Assembly and Stacking of Flow-through Enzymatic Bioelectrodes for High Power Glucose Fuel Cells; ACS Applied Materials & Interfaces, vol. 9, No. 28; dated Jun. 28, 2017; pp. 23836-23842.

Sakai, Hideki, et al.; "A high-power glucose/oxygen biofuel cell operating under quiescent conditions"; Energy Environ. Sci., vol. 2; dated Sep. 29, 2008; pp. 133-138.

Reuillard, Bertrand, et al.; "High power enzymatic biofuel cell based on naphthoquinone-mediated oxidation of glucose by glucose oxidase in a carbon naotube 3D matrix"; Phys. Chem. Chem. Phys, vol. 15; dated Feb. 25, 2013; pp. 4892-4896.

* cited by examiner

BIOCELL WITH FUEL RESERVOIR

FIELD OF THE INVENTION

The invention relates to an enzymatic fuel cell, or biocell, to its uses for the detection or oxidation of a biofuel such as glucose, to kits comprising it as well as to electrical or electronic devices incorporating said biocell. The invention also relates to methods of manufacturing this biocell as well as to assemblies comprising at least two biocells according to the invention.

PRIOR ART

Fuel cell technology is based on the conversion of chemical energy into electronic energy. An organic molecule such as glucose is one of the most important sources of energy for many living organisms and can be considered a safe, easy to handle, and consumable, and therefore biodegradable, biofuel.

Biofuel enzyme cells (also called biocells) use enzymes to produce energy or electrical power from biological substrates such as oxygen, methanol, glucose or starch. Biocells convert biofuel in the presence of enzymatic compounds, which produces power. The most well-known biocells work by oxidation of glucose (GBFC) are such cells which convert glucose by oxidation at the anode for the production of power using an enzyme incorporated therein and having a catalytic function of the reaction. The function of the cathode is generally to reduce oxygen and may or may not include an enzyme which catalyzes this reaction.

Enzymes are promising alternatives to noble metal catalysts since most of them are operational at neutral pH and at room temperature and offer little or no toxicity, which is not the case with other metal-based catalysts. Thus, such biofuel biocells can be very easily recycled and present ecological alternatives as an electric current generator, in particular for disposable devices.

The present invention relates more particularly to the manufacture of a "button" type biocell, that is to say of small size and capable of providing electricity equivalent to a metal-based button cell and which can optionally be thrown away without risk for the environment. This is not the case with button cells and alkaline batteries today. This green technology could provide an original solution to the problems associated with recycling zinc, lithium or manganese-based batteries used on a daily basis. Without the presence of metals, the device according to the invention also describes a portable energy source invisible to metal detectors.

Alternatively or additionally, the device according to the invention aims to allow the production of electrical energy for a specific need when other conventional energy sources (wind, solar, etc.) are not available. Indeed, the enzymes have a unique selectivity which allows the production of power in complex media which can allow the use of liquid and in particular of various biological fluids: sugar (glucose), sugary drinks, physiological fluids (saliva, blood, urine), of animal or vegetable origin (fruit juice) etc.) as an activator and/or fuel. In this context the term "fuel" and "biofuel" is interchangeable.

In these respects, important challenges must be overcome before being able to put such biofuel cells into commercial application.

In particular, they should preferably be small (1 to 5 cm$^2$ in area), or even very small (less than 0.5 cm$^2$ in area) in size, and be designed to be able to replace batteries of the "button" type frequently used in disposable devices. They should advantageously be easily recyclable, and preferably inexpensive.

Thus, the invention aims in particular to solve the problem of providing a biofuel cell, in particular of a design allowing its use in disposable devices, which is inexpensive (button cell type) or designed for single-use, preferably of small dimensions, and advantageously allowing optimized access of the fuel and the oxidant to the electrochemical cell, to produce the maximum amount of energy. In addition, it is advantageous that this biofuel cell can be used in an assembly of several biofuel biocells or electrochemical cells, to produce sustainable and renewed energy.

Thus, in general, the invention aims to solve the problem of the easy and low-cost manufacture of biocells and their integration into more or less sophisticated electrical circuits in which the current densities produced are sufficiently high to operate said devices. Advantageously, the voltage delivered is sufficient to operate devices reliably.

DESCRIPTION OF THE INVENTION

According to one embodiment, the invention comprises a biocell with a biofuel reservoir, being intended to be brought into contact with a liquid medium, said liquid medium optionally comprising a biofuel, and a fluid medium comprising an oxidant, said biocell comprising a first electrochemical cell, said first electrochemical cell comprising:
  an anode made of a solid agglomerate comprising a conductive material mixed with a first enzyme capable of catalyzing the oxidation of the biofuel; and
  a cathode consisting of a solid agglomerate comprising a conductive material mixed with a second enzyme capable of catalyzing the reduction of the oxidant, and
  a separating and porous membrane, electrically insulating, and permeable to said liquid medium, placed between the anode and the cathode.

Said biocell further comprises means for electrically switching on said biocell with an electrical receiver, said electric switching means allowing current to flow between the anode and the cathode. The biocell is characterized in that it comprises a means for storing the biofuel and making the liquid medium available to the anode, said means comprising a hydrophilic porous material in contact with said anode and having a surface mass of 500 to 900 g/m$^2$.

The storage means can therefore act as a reservoir for biofuel and/or a liquid containing it. Preferably, the storage means has a surface mass (or grammage) which can range from 650 to 750 g/m$^2$ so as to be sufficiently absorbent. Advantageously, its surface weight is 703 g/m$^2$, optionally ±20%. It can in particular be chosen from the group of values consisting of 655, 660, 665, 670, 675, 680, 685, 690, 695, 696, 697, 698, 699, 700, 701, 702, 703, 704, 705, 707, 708, 709, 710, 711, 712, 713, 714, 715, 720, 725, 730, 735, 740, 745, 750, 755 and 760 g/m$^2$. Thus the storage medium is a very porous material.

The storage means may be in the form of a porous pad, a pad or, in English "pad", The material constituting the storage means is preferably an electrical insulator. This material can include or be made up of woven fibers, or non-woven fibers (felt). These fibers are preferably natural and/or biodegradable fibers, for example they may be a material comprising, or consisting essentially of, or else based on cellulose, and in particular cotton. It can also be a natural polymer (cellulose, cotton, sponge, chitosan, etc.) or a synthetic (polyacrylic foam, polyvinyl alcohol, etc.). The expression "based on X" can be interpreted as referring to a material consisting of more than 90% by mass, preferably more than 95%, or even more than 98% relative to the total mass of component X. Storage means can therefore advantageously comprise, or be essentially constituted, of a sheet of paper, preferably of the blotter type, for example of super-thick blotter. It is also preferred that this pad and/or the sheet of paper be without additives. The grammage can be measured according to standard NF EN ISO 536 November 2012.

The thickness of the storage means is advantageously as small as possible to allow miniaturized use. However, for other uses, this thickness can be more substantial and of the same order of a centimeter, or half a centimeter. This thickness can therefore be from 1 cm to 0.1 mm, preferably from 8 to 2 mm, and more particularly around 2.6 mm, optionally ±20%. It can in particular be selected as being a thickness chosen from the group consisting of 1; 1.5; 1.6; 1.7; 1.8; 1.9; 2; 2.1; 2.2; 2.3; 2.4; 2.6; 2.7; 2.8; 2.9; 3; 3.1; 3.2; 3.3; 3.4; 3.5; 3.6; 3.7; 3.8; 3.9 and 4 mm.

Advantageously, the storage means is a sheet of blotting paper, with a thickness of 2.6 mm±0.2 mm. Its porosity must allow good absorption of the liquid containing the fuel (for example water, urine, sugary drink, blood, etc.) and in particular sugar. According to a preferred variant of the invention it must be sufficiently rigid for the embedding or the maintenance of bioanodes or biocathodes.

Advantageously, the storage means has a liquid filtration time which can range from 100 to 140 s/ml, preferably from 110 to 130 s/ml and advantageously around 120 s/100 ml, optionally ±20%; measured according to the Herzberg method (with a water column of 100 mm).

The electrochemical cell included in the biocell according to the invention comprises an anode and a cathode. These electrodes are in the form of a solid agglomerate which comprises at its base a preferably porous conductive material and at least one enzyme of the half-reaction to be catalyzed. This porous material can be any recyclable porous conductive material such as carbon felt, microporous carbon, carbon nanotubes, activated carbon, carbon black, conductive polymers, etc. In the examples, pellets based on single-walled or more advantageously multi-walled carbon nanotubes (MWCNT) or on carbon black offer excellent porosity associated with excellent conductivity. By "carbon nanotube" it is meant a carbon nanotube of which at least one dimension is less than 1500 nm. Preferably, the carbon nanotubes have a length (L)/diameter ratio denoted L/diameter of between 100 and 5000. Preferably, the carbon nanotubes have a length of approximately 1.5 μm and for example a diameter of approximately 10 nm.

In the exemplary embodiments of the invention of the application, the biofuel chosen is glucose, due to the great availability of this compound and its little impact on the environment. However, the structure of the biocell according to the invention can adapt to substrates other than glucose insofar as the associated enzymatic compounds are also suitable.

The theoretical reaction balance of the glucose/O2 enzyme biocell is as follows:

Anode: glucose→gluconolactone+2H$^+$+2 e$^-$
Cathode: O2+4H$^+$+4 e→2H2O
Biocell: 2 glucose+O2→2 gluconolactone+2H2O Thus, according to a preferred aspect of the invention, an enzymatic system used at the anode can comprise at least one glucose oxidase. Glucose oxidases (GOx) are oxidoreductase enzymes of the EC 1.1.3.4 type (April 2018 classification) which catalyze the oxidation of glucose, more particularly β-D-glucose (or dextrose) into hydrogen peroxide and D-glucono-δ-lactone, which then hydrolyzes to gluconic acid. Glucose oxidases bind specifically to β-D-glucopyranose (hemiacetal form of glucose) and do not act on l'α-D-glucose. They are however able to act on glucose in its enantiometric forms, because in solution glucose mainly adopts its cyclic form (at pH7: 36.4% α-D-glucose and 63.6% β-D-glucose, 0.5% in linear form). In addition, the oxidation and consumption of the β form shifts the α-D-glucose/β-D-glucose balance towards this form. The term GOx extends to native proteins and their derivatives, mutants and/or functional equivalents. This term extends in particular to proteins which do not differ substantially in structure and/or in enzymatic activity.

Glucose oxidases include and require a cofactor to enable catalysis. This co-factor is Flavin Adenine Dinucleotide (FAD), a major oxidation-reduction component in cells. FAD serves as an initial electron acceptor, it is reduced to FADH$_2$ which will be re-oxidized to FAD (regeneration) by molecular oxygen (O$_2$), which is more reducing than FAD). The O$_2$ is finally reduced to hydrogen peroxide (H$_2$O$_2$), The cofactor is included in the commercially available GOx enzyme and the term GOx and FAD-GOX are equivalent.

The most widely used glucose oxidase is that extracted from *Aspergillus niger*. However, GOx from other sources can be used, such as for example certain strains of the species *Penicillium* or of *Aspergillus terreus*.

Glucose oxidase from *Aspergillus niger* is a dimer composed of 2 equal subunits with a molecular weight of 80 kDa each (by gel filtration). Each subunit contains a flavin adenine dinucleotide and an iron atom. This glycoprotein contains approximately 16% neutral sugar and 2% amino sugars. It also contains 3 cysteine residues and 8 potential sites for N-glycosylation.

The specific activity of GOx is preferably greater than or equal to 100,000 units/g solid (without addition of O$_2$). One unit is defined as the oxidation capacity of 1.0 μmole of β-D-glucose to D-gluconolactone and H2O2 per minute at pH 5.1 at 35° C. (Km=33-110 mM; 25° C.; pH 5.5-5.6).

Insofar as the use of GOx involves the production of hydrogen peroxide, catalase can be added to the enzymatic system.

Catalase is a tetrameric enzyme catalyzing the reaction: 2H$_2$O$_2$→O$_2$+2H$_2$O. Each subunit contains iron bound to a protoheme type IX group. Each subunit is equivalent and comprises a polypeptide chain of approximately 500 amino acids. The molecular weight of each subunit is generally 60 kDa (gel filtration). Catalase can bind strongly to NADP and NADP and the heme group are then positioned 13.7 Å from each other. It can react with other hydrogenated alkyl peroxides such as methyl peroxide or ethyl peroxide. The activity of catalase is generally constant over a pH range of 4 to 8.5. Its specific activity is preferably greater than 2000 units/mg, in particular greater than 3000 units/mg, for example approximately 5000 units mg of proteins. One unit is defined as the capacity to decompose 1.0 micromole of hydrogen peroxide (H$_2$O$_2$) per minute at pH 7.0 at 25° C. the H$_2$O$_2$ concentration preferably falling from 10.3 to 9.2 millimolar. The term catalase extends to native proteins and their derivatives, mutants and/or functional equivalents. This term extends in particular to proteins which do not differ substantially in structure and/or in enzymatic activity. The catalase used is preferably of bovine origin.

It is also possible to use other enzymes which transform glucose, and particularly at least one dehydrogenase. In fact, hydrogen peroxide is not produced during the reaction catalyzed by this enzyme, which is advantageous. Dehydrogenases also work in combination with FAD (see above). A particularly preferred dehydrogenase is Flavine Adenine Dinucleotide-Glucose Dehydrogenase (FAD-GDH) (EC 1.1.5.9). The term FAD-GDH extends to native proteins and their derivatives, mutants and/or functional equivalents. This term extends in particular to proteins which do not differ substantially in structure and/or in enzymatic activity. Thus, to produce the anode of the electrochemical cell of the biocell according to the invention, in combination with a cofactor, a GDH enzymatic protein having an amino acid sequence having at least 75%, preferably 95%, and even more preferably 99% identity with the GDH sequence (s) as listed in the databases (for example SWISS PROT), can be used. An FAD-GDH of *aspergillus* sp. is particularly preferred and effective, but other FAD-GDHs from *Giornerella cingulata* (GcGDH), or a recombinant form expressed in *Pichia pastoris* (rGcGDH), could also be used. The FAD-GDH used in an exemplified embodiment is an FAD-GDH from *Aspergillus* sp. (SEKISUI DIAGNOSTICS, Lexington, Mass., No, Catalog GLDE-70-1192) which has the following characteristics:

Appearance: lyophilized yellow powder.
Activity: >900 U/mg powder 37° C.
Solubility: readily dissolves in water at a concentration of: 10 mg/mL.
A unit of activity: quantity of enzyme that will convert one micromole of glucose per minute at 37° C.
Molecular Weight (Gel Filtration) 130 kDa.
Molecular Weight (SDS Page): diffuse 97 kDa band indicative of a glycosylated protein.
Isoelectric point: 4.4.
K=value: $5.10^{-2}$ M (D-Glucose), The porous conductive material can also comprise an aromatic molecule acting as a redox mediator, such as 1,4-naphthoquinone, to improve electronic exchanges. Other molecules selected from the group formed by 9,10-phenanthroline, 1,10-phenanthroline-5,6-diene, 9,10-anthraquinone, phenanthrene, 1,10-phenanthroline, 5-methyl-1,10-phenanthroline, pyrene, 1-aminopyrene, pyrene-1-butyric acid, and mixtures of two or more of these can also be considered. The use of such compounds proves to be particularly advantageous in the case of enzymatic systems comprising an FAD-GDH or a GOx.

The oxidant of the biofuel cell can advantageously be molecular oxygen, and in particular oxygen contained in the air.

When the oxidant is molecular oxygen $O_2$, the enzymatic system which can be used at the cathode can advantageously comprise a bilirubin oxidase (BOD). BOD is an oxidoreductase enzyme (EC Classification 1.3.3,5, CAS number 80619-01-8; April 2018) which catalyzes the reaction:

2 bilirubin+O(2)<=>2 biliverdin+2H(2)O.

The most widely used bilirubin oxidase is that extracted from *Myrothecium verrucaria*. However, the use of BOD from other sources may be considered. The activity of BOD is advantageously greater than 15 units/mg of protein, preferably greater than 50 units/mg, for example around 65 units/mg of protein. One unit is defined as the ability to oxidize 1.0 micromoles of bilirubin per minute at pH 8.4 at 37° C. The term BOD extends to native proteins and their derivatives, mutants and or functional equivalents. This term extends in particular to proteins which do not differ substantially in structure and/or in enzymatic activity.

Protoporphyrin IX (CAS number 553-12-8; April 2018), is a compound with a porphyrinic unit of the crude formula $C_{34}H_{34}N_4O_4$. It is used to functionalize the porous conductive material, and in particular the nanotubes, and allow better orientation of enzymes such as BODs. It is therefore advantageously included in the material constituting the cathode.

The solid agglomerate which combines a porous conductive material and at least one enzyme and/or one enzymatic system is preferably in the form of a block or of a pellet, for example circular, advantageously obtained by compressing the mixture of elements. The agglomerate can be obtained easily by compression and take any particular shape desired. In particular, the bioanodes and/or biocathodes according to the invention can take the form of small (1 to 2 cm in diameter), or even very small (less than 0.5 cm in diameter), pellets, for example circular or polygonal. Such pellets can have a thickness varying from 3.5 mm to 0.2 mm, for example 0.25 mm. As a result, the biocell according to the invention can be of varied shape and of small size. In particular, it can occupy only a volume less than or equal to 2 cm$^3$, preferably less than or equal to 1 cm, or even less than or equal to 0.75 cm$^3$. It may in particular be designed to be able to replace "button type" batteries.

According to a particularly preferred aspect of the invention, the anode therefore comprises a GOx enzyme, preferably combined with a catalase, or an FAD-GDH enzyme. In this case, the biofuel is therefore glucose. In both cases, the bioanode also comprises a glucose oxidation mediator, for example a 1,4-naphthoquinone compound. Preferably, the biocathode comprises an enzyme reducing oxygen, and more particularly BOD, advantageously combined with protoporphyrin IX, The terms biocathode and bioanode refer to the presence of biological material, for example an enzyme, in their structure. In the context of the biofuel cell of the invention, they are to be used in a manner equivalent to cathode and anode.

The device according to the invention comprises a separating and porous membrane, electrically insulating, and permeable to the liquid medium, which is placed between the anode and the cathode. This membrane allows the passage in particular of ionic species between the anode and the cathode.

According to a particular variant of the invention, this membrane can be a thin sheet (less than 200 μm thick) of paper, which has a low surface weight (for example less than or equal to 150 g/m$^2$. In particular, such a membrane has a thickness of less than 150 μm, preferably less than 100 μm, preferably less than 75 μm of paper, which is advantageously biodegradable. This option is particularly preferred when the means for storing the biofuel and making the liquid medium available to the anode surround and support the bioanode and/or the anode pellets, and optionally biocathode (s) of the biocell.

According to another preferred variant of the invention, the separating and porous membrane, electrically insulating, and permeable to the liquid medium, is also the means for storing the biofuel and making the liquid available. Advantageously, this storage means is as described above.

The biocell according to the invention also comprises switching means which generally incorporates an electrically conductive material. These means can be in the form of layers, tongues or threads. Such a layer, tongue or wire advantageously has a low thickness, a high thermal and/or electrical conductivity and can comprise, or be (substantially) made of, highly oriented graphite. Thus, it is possible to use a sheet, or a tab, of pyrolytic graphite (pyrolytic graphite sheet). Its thickness can be chosen as ranging from 10 to 500 μm, preferably from 17 to 300 μm, and advantageously from 40 to 100 μm. It can be chosen from the group consisting of thicknesses of 10, 17, 25, 40, 50, 70, and 100

μm. Its thermal conductivity (in the longitudinal plane of the sheet) may be 500 to 2000 W/(mK), preferably 700 to 1950 W/(mK) and advantageously 900 to 1350 W/(mK). It can be chosen from the group consisting of thermal conductivity values of 700, 1000, 1300, 1350, 1600, 1850 and 1950 W/(mK). This layer may also have an electrical conductivity greater than 5.000 S/cm, preferably greater than or equal to 8,000 S/cm, for example around 10,000 S/cm. However, it may have a higher conductivity, for example around 20,000 S/cm, in particular if the thickness of the layer is less than 40 μm. This layer can also have heat resistance, for example resistance to a temperature of more than 200° C., advantageously of more than 300° C., for example of about 400° C.

The device according to the invention advantageously comprises an external coating which may be a protective layer, or film, which partially covers the electrochemical cell (s) of the device. This is preferably flexible, adhesive, non-toxic, chemically stable, electrically insulating, insensitive to radiation and/or has a wide operating temperature range (for example from −150° C. to 200° C., or even around temperature of 260° C. This coating, or outer protective film, can comprise, or be (substantially) made of a glass fiber fabric impregnated with a relatively inert material such as a perfluorinated polymeric material of the PTFE (polytetrafluoroethylene) type or a silicone-based material. The PTFE can be Teflon® from Du Pont de Nemours, Fluon® from Asahi Glass, Hostaflon® from Dyneon. The film or coating is preferably impregnated with more than 50% by weight of said material, advantageously from 50 to 70%, preferably from 57 to 64% relative to the total weight of the film. Its thickness may be a few tenths or even hundredths of a millimeter. For example, it can be chosen from a range of 0.03 to 0.50 mm, preferably 0.05 to 0.30 mm and preferably 0.06 to 0.14 mm, for example be 0.07 mm (NF EN ISO 2286-Dec. 3, 2016), According to a preferred aspect of the invention, the coating, or protective film, comprises an adhesive layer, preferably water resistant, allowing it to adhere to the external surface of the electrochemical cell (s) of the biocell according to the invention. According to one particular aspect, this film can be affixed directly to one face of the anode and/or of the cathode, or directly to part of the circuitry means. According to another preferred aspect, this outer covering, which is preferably flexible and insulating, comprises one or more openings positioned and dimensioned so as to allow the access of a liquid and or a gas at the anode and/or the cathode. This opening can be precut in the coating: for example it can take the form of a series of small circular openings positioned opposite the biocathode. Additionally or alternatively, this opening can be formed by the fact that the coating does not completely surround the biocell comprising the electrochemical cell (s) and the storage means, but leaves an opening giving access to these elements. Thus, for a device of a generally planar shape, an opening can be left on the edge of the device.

According to an advantageous aspect of the invention, when the bioanode and/or the biocathode (which may be in the form of a pellet or of a button), is kept in a frame, said frame being either said means for storing biofuel and makimg of the liquid medium available, or an electrically insulating material such as PTFE.

Thus, according to a first embodiment, the anode is inserted into the storage means, which may for example be a sheet of absorbent material as described above. This storage means will therefore also act as a frame and/or support and maintain the bioanode and possibly the biocathode, in position, and, being generally in direct contact with the latter, will keep it in contact with the liquid medium and the biofuel contained therein. According to this variant of the invention, the device can comprise several electrochemical cells of the type described in the application, said electrochemical cells being connected serially. Such a device therefore consists of a stack of electrochemical cells, the number of cells generally not being greater than ten. For example three or four individual cells can be stacked.

According to another embodiment described above, the storage means is also the membrane of the biocell. In this case, the anode (and possibly the cathode) can be inserted into a frame, or jig, composed of an insulating material, such as for example PTFE (polytetrafluoroethylene). This frame preferably has openings sized to receive the bioelectrode (s) and make it possible to hold and/or position the electrode (anode or cathode). Indeed, according to this variant of the invention, the frame may contain several electrodes which may be of the anode or cathode type. The frames are dimensioned to make it possible, when two frames are placed opposite each other, to put an anode and a cathode opposite each other and thus to create several electrochemical cells. The switching means are then advantageously positioned to connect these electrochemical cells serially.

An object of the invention is also a method of manufacturing a biocell as described in the present application. This method comprises the use of an external coating sheet as described and comprises the step of positioning on an internal face, preferably adhesive, of the external coating, the means for switching on, at least one electrode (bioanode or biocathode) facing said switching means, the storage means and possibly the membrane. The outer covering sheet is dimensioned so that once the elements of the biofuel cell are positioned on the adhesive surface, a free surface is present around the periphery of these elements. This free surface is positioned and sized to allow these elements to be joined together and to constitute the biocell.

According to a variant of the method according to the invention, the switching means are positioned firstly on the internal face of the coating and then the frame (or template) is superimposed. Secondly, a mixture in the form of powder or paste constituting an anode or a cathode according to the invention is positioned inside the opening of the frame and this assembly is subjected to a compression in-situ to obtain a solid agglomerate constituting the anode or the cathode. This step can be repeated to form the missing electrode (cathode or anode) and the two coatings are assembled, once the storage means is positioned between these layers, to form the biocell according to the invention. These two parts are advantageously joined by the presence of an adhesive on the internal part of the external coating.

The invention also relates to a biocell as described in the present application and further comprising an aqueous liquid, said liquid optionally comprising a biofuel. Indeed, the biofuel may already be present in the device in a dry and/or solid and or non-solubilized form and/or capable of migrating to the enzymatic sites. For example, it can be incorporated into, or positioned near, fuel storage means. When water (pure or not) is added, the biofuel thus present (for example sugar) is dissolved in the medium which allows electrochemical exchanges to take place. Alternatively or additionally, the added liquid comprises the biofuel. This can be, for example, a physiological liquid such as blood, urine or saliva or an alcoholic or glucose drink.

An object of the invention is also a process for obtaining a biocell comprising placing a biocell according to the invention as described in the present application in the presence of a liquid, preferably an aqueous liquid, optionally comprising a biofuel such as glucose, starch or ethanol.

Another object of the invention is an apparatus comprising a biocell according to the invention, and an electrical receiver (that is to say an apparatus which uses (receives) electric current), said biocell being electrically connected to said electrical receiver. Such an apparatus can be a test, in particular a test of the biological fluid: for example a pregnancy test or a blood sugar test. Alternatively or additionally, the biocell (and or the device) according to the invention can be incorporated into an electronic device with electronic display and/or light emission. More generally, the device according to the invention is of the type operating with button type batteries using metallic derivatives. Such an apparatus according to the invention can advantageously be disposable and/or biodegradable.

Another subject of the invention is a kit for the manufacture of a biocell as described in the present application and which comprises a biocell as described in the present application, associated with instructions for use and possibly a container comprising an aqueous liquid as described above.

Another object of the invention is the use of a thick blotting paper as described above for the manufacture of a biocell or the manufacture of a device for obtaining a biocell, preferably a biocell according to the invention. Preferably the blotting or absorbent paper is 2.6 mm±0.2 mm thick.

Another object of the invention is the use of a biocell according to the invention for the generation of an electric current.

EXAMPLES

Reagents

Glucose oxidase type VH (GOx) from *Aspergillus Niger* (April 2018: No. EC: 1.1.3.4, No. CAS: 9001-37-0, molecular weight: 160 kDa (gel filtration)>100,000 units/g) comes from the company Sigma-Aldrich (Product code G2133).

Catalase from bovine liver (April 2018: No. EC: 1.11.1.6, No. CAS: 9001-05-2, molecular weight 250 kDa, 2000 to 5000 units/mg) also comes from the company Sigma-Aldrich Co. (product code C1345). Bilirubin oxidase (BOD) from *Myrothecium Verrucaria* (April 2018 EC No. 1.3.3.5, CAS No: 80619-01-8. 15-65 units/mg) was obtained from Sigma Aldrich (product code B0390).

95% pure protoporphyrin IX also comes from Sigma-Aldrich Co. (product code P8293).

Flavin adenine dinucleotide-dependent glucose dehydrogenase (FAD-GDH, 11580 Unit/mg solid (one unit of activity: amount of enzyme that will convert one micromole of glucose (β-Dextrose) per minute at 37° C.)) of *aspergillus sp.* (April 2018: EC No. 1.1.5.9) comes from the company SEK SUI. The multi-walled carbon nanotubes (MWCNT) were purchased from the company Nanocyl (purity>95%, diameter 10 nm, length 1.5 µm).

VULCAN® brand carbon black XC72R was purchased from CABOT corporation.

The current collecting microporous gas diffusion (GDL) layer was purchased from Paxitech. It consists of a narrow mesh of carbon fibers in the form of a carbon felt and has a thickness of 210 µm, a through resistivity of 8 mΩcm² and a through permeability to air of 70 seconds.

The porous paper used as a pad is super thick blotting paper (grade 707) purchased from VWR reference 732-0604. This is a 100% cotton blotting paper, without additives, and made with Ultrapure water. Its texture is smooth and regular and its structure homogeneous. Its surface mass is 703 g/m² for a thickness of 2.6 mm. its given technical characteristics are a filtration time (according to Herzberg) of 120 s/100 ml (with a water column of 100 mm) as well as a rise of 75 mm in 96 seconds according to the Klemm test (capillary penetration rate).

The 140 µm thick cellulose sheet used is of the Whatman type (qualitative filter paper for technical use, Grade 0903) distributed by Sigma Aldrich (ref WHA10334885).

The protective film is an adhesive sheet of a fabric or glass film impregnated with PTFE (TISOFLON 3 AD; ISOFLON company) 70 µm thick and having a PTFE impregnation rate of 61% by weight. The adhesive surface of this film is covered with a protective PTFE (Teflon™) sheet. This film is covered with a protective Teflon sheet which can serve as a holding frame or template for the bio-anodic and/or bin-cathodic pellets according to the invention.

The enzymes were stored at −20° C. Distilled water was obtained by purifying water to a resistivity of 15 MΩ×cm using a Millipore Ultrapure™ system. The high purity oxygen and argon come from the MESSER company. The glucose solutions were left to transform into β-D-glucose overnight before use. All the other reagents, including 1,4-naphthoquinone, come from Sigma-Aldrich Inc. For the electrochemical characterization of the biofuel cell, the anode was defined as the working electrode while the cathode was connected as the reference electrode. All experiments were performed with a glucose solution of 5 (close to the concentration of certain body fluids) or 150 mmol L−1 in McIlvaine or phosphate buffer, at pH 7. The solution was dropped onto the edge of the reservoir, at least on one which was not completely covered with an insulating coating. The biocell was connected to a Biologic® VMP3 multichannel potentiostat running EC-lab 10.39 software. The polarization and power curves were recorded after a 30 second discharge. All the experiments were performed at room temperature (approx. 20° C.).

The biocathodes and bioanodes exemplified below are solids shaped into compressed discs.

Example 1 (Pellets Inserted into a Porous Sheet)

For the biocathode, the carbon nanotubes (MWCNT) were mixed with protoporphyrin IX in the presence of DMF (Dimethylformamide) then heated at 80° C. for approximately 12 hours, Protoporphyrin IX promotes the orientation of enzymatic proteins relative to nanotubes. The nanotubes thus functionalized were rinsed and filtered several times with distilled water. 35 mg of MWCNT functionalized with protoporphyrin IX were ground in the presence of 15 mg of BOD and 100 μl of distilled water.

For a bioanode, 35 mg of MWCNT, 15 mg of GOx, 10 mg of catalase from bovine liver and 5 mg of 1,4-naphthoquinone were ground with 100 μL of distilled water. For another bioanode based on FAD-GDH, 35 mg of functionalized MWCNT, 15 mg of FAD-GDH and 5 mg of 1,4-naphthoquinone were ground with 100 μL of distilled water.

Each homogeneous paste is then compressed respectively on an electrical contact GDL tab using a hydraulic press to obtain a pellet 1 cm in diameter and 2 mm in thickness. In this case, this 9 or 9' GDL tongue serves both as a current collector and as a support for compressing the carbon paste.

Figure 1:
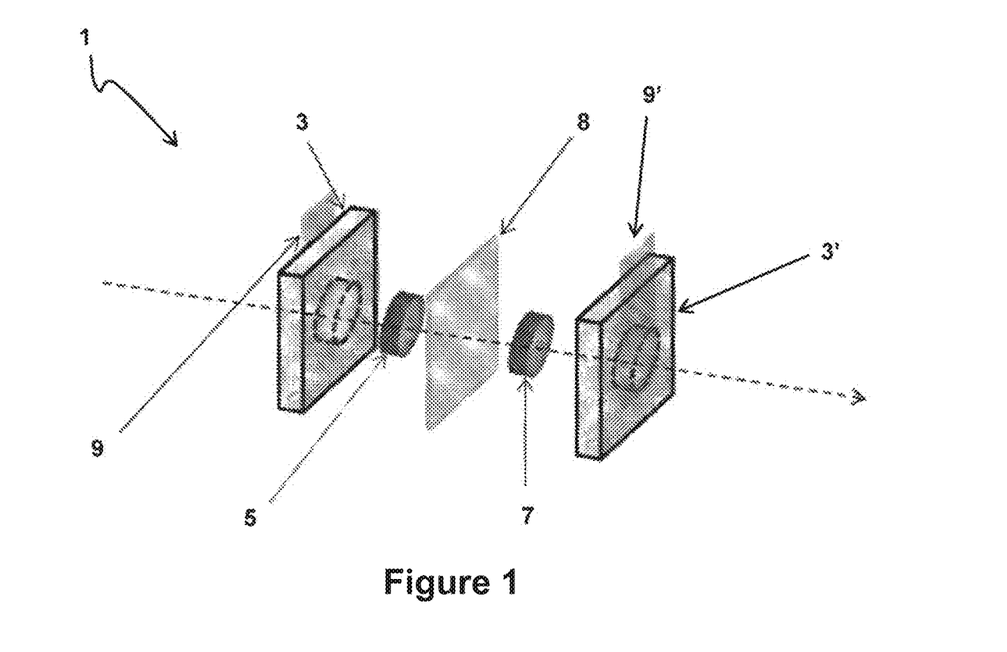
FIG. 1 is a partial exploded view of a device according to the invention as described in Example 1.

Holes of dimensions and shapes corresponding to those of the anode and cathode pellets are made in a pad (a sheet of blotting paper) 2.6 mm thick and 25 mm×25 mm in size. Each pad, or "pad", will serve as a frame for a pellet. The biocell device is then assembled: each of the pellet/tab associations produced is positioned inside the openings of the pads from the rear thereof so as to position the GDL tabs on the outside and protruding relative to their respective pad. A bioanode and a biocathode are thus formed. A thin sheet of Whatman cellulose acting as an electrical insulator is placed between the bioanode and the biocathode. This assembly forms the basis of the electrochemical cell. FIG. 1 is a semi-exploded view of such a device. An enzyme pellet 5, or bioanode, comprising GOx or FAD-GDH, is positioned in fuel tank 3, the GDL tab 9 protruding from the rear. Symmetrically, an enzyme pellet 7, or biocathode, comprising BOO is positioned in a 3' pad, the 9' GDL tab also protruding from the rear thereof. The porous sheet of electrical insulation 8 is placed between the bioanode 5 and the biocathode 7 and their respective frames 3 and 3'.

This device is then enveloped by an adhesive protective film of glass fabric and PTFE 70 μm thick (not shown) which covers the back of the two electrodes. The protruding GDL tab portions are not substantially covered with this protective film. In addition, 4 holes of 2 mm in diameter made in the protective film are positioned at the back of the biocathode and allow the diffusion of oxygen from the air inside the device and its provision to the biocathode. 7.

Figure 2:
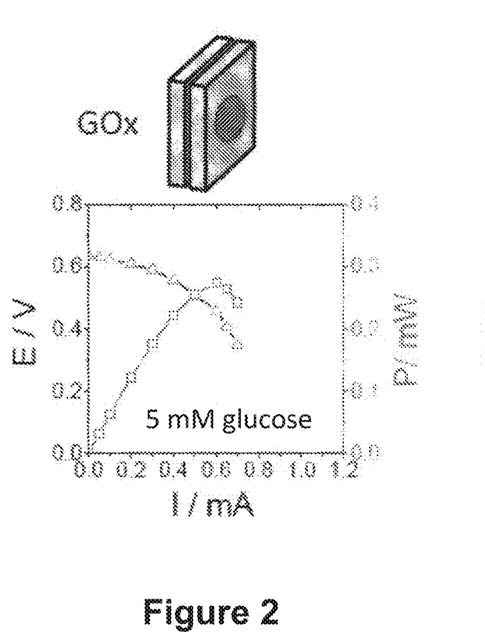
FIG. 2 represents the polarization and power curves of a GOx/BOD biocell according to Example 1, produced using the device of Example 1 and a 5 mM glucose solution.
Figure 3:
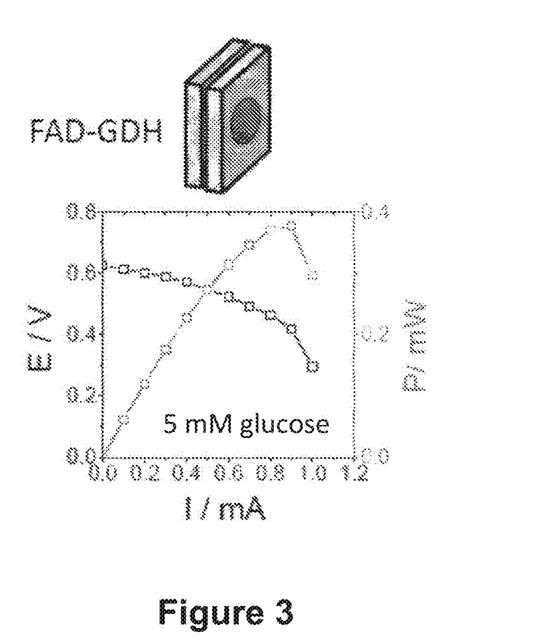
FIG. 3 represents the polarization and power curves of an FAD-GDH/BOD biocell according to Example 1, produced from the device according to the invention of FIG. 1 and from a solution of 5 mM of glucose.

FIGS. 2 and 3 represent the polarization and power curves of the GOx Biopiles (FIG. 2) and FAD-GDH (FIG. 3). The powers obtained in the case of FAD-GID (0.38 mW) are greater than the powers obtained in the case of GOx (0.27 mW). This is due to the fact that FAD-GDH is more active than GOx and that it does not generate $H_2O_2$ as a co-product. In fact, $H_2O_2$ can increase the instability of the cell and inhibit the activity of the BOD enzyme at the cathode.

Example 2: Stacking

Figure 4:
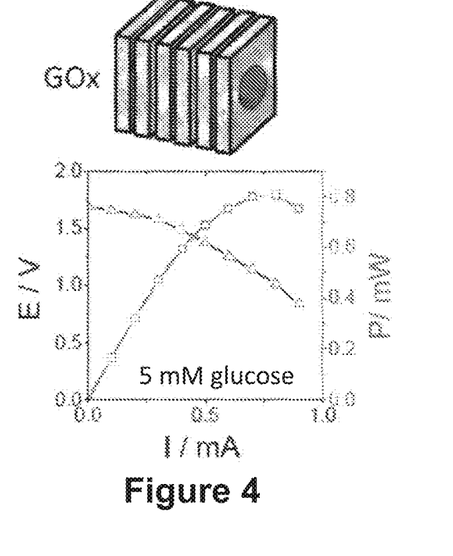
FIG. 4 represents the polarization and power curves of a GOx/BOD biocell according to the embodiment of Example 2, the fuel being a solution of 150 mM of glucose.

A stack of 3 cells with an FAD-GOX BOO biocathode/anode is shown schematically (GDL tabs not shown) in FIG. 3 and FIG. 4. This stacking was produced by leaving only the outer tabs protruding so as to close the circuit. Once the cells were juxtaposed, the stack was covered with an adhesive film made of glass fiber and PTFE fabric in the same way as the device of Example 1.

Figure 5:
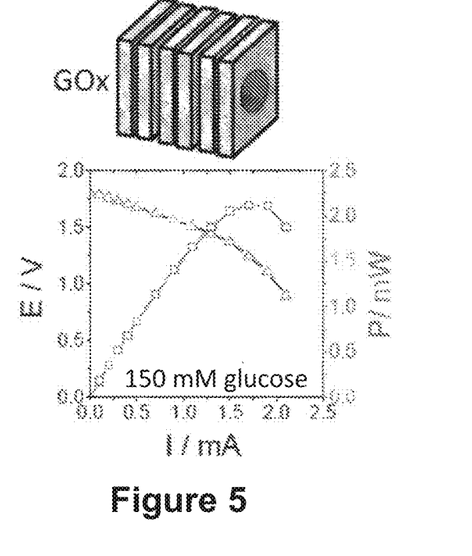
FIG. 5 represents the polarization and power curves of a GOx/BOD biocell according to the embodiment of Example 2, the fuel being a solution of 150 mM of glucose.

This example shows the ease of stacking of these batteries, going from 0.27 mW and 0.62 V of fem for a single battery to 0.82 mW and 1.7 V of fem for a stack of 3 batteries with a pad soaked in a 5 mM glucose solution (FIG. 4). A concentrated glucose solution (150 mM) gives access to high powers of 2.2 mW (FIG. 5). FIGS. 4 and 5 show the effect of these two different glucose concentrations on the performance obtained.

Example 3: FAD-GDH BOD Biocell Using Carbon Black Support

In order to overcome the problems that can be linked to carbon nanotubes in terms of access to commercial samples or their suspicion of toxicity, MWCNTs have been replaced by carbon black, already used in many commercial products.

Figure 6:
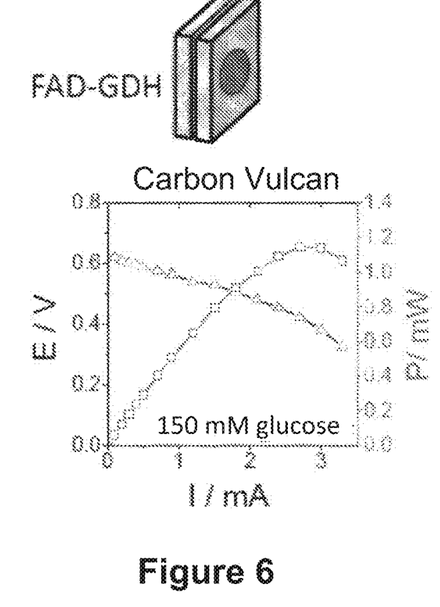
FIG. 6 represents the polarization and power curves of an FAD-GDH/BOD biocell on Vulcan® carbon produced according to Example 3, the fuel being a solution of 150 mM of glucose.

Enzymatic pellets are obtained using the same process as Example 1 but replacing the MWCNTs with carbon black (Vulcan®). A 1-cell biocell is then produced also using the method of Example 1. FIG. 6 represents the polarization and power curves for this FAD-GDH biocell on Vulcan® Carbon obtained when placed in the presence of a 150 mM glucose solution.

Figure 7:
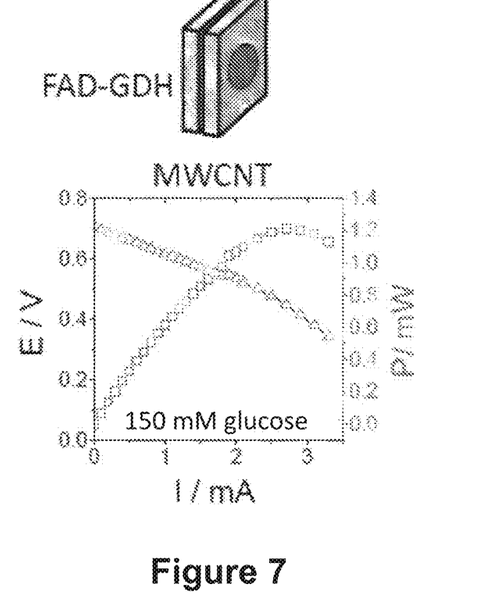
FIG. 7 represents the polarization and power curves of an FAD-GDH/BOD biocell on MWCNTs produced according to Example 1, the fuel being a solution of 150 mM of glucose.

FIG. 7 represents the polarization and power curves of the FAD-GDH biocell on MWCNT of Example 1 when brought together with a glucose solution of the same concentration (150 mM). The powers delivered by batteries based on MWCNTs and Vulcan carbon (carbon black) are respectively 1.3 and 1.2 mW for a glucose recharge of 150 mM (in approximately 0.5 mL). The two materials provide access to similar powers and can therefore both be used depending on the technical and environmental constraints necessary for the manufacture of these batteries.

Figure 8:
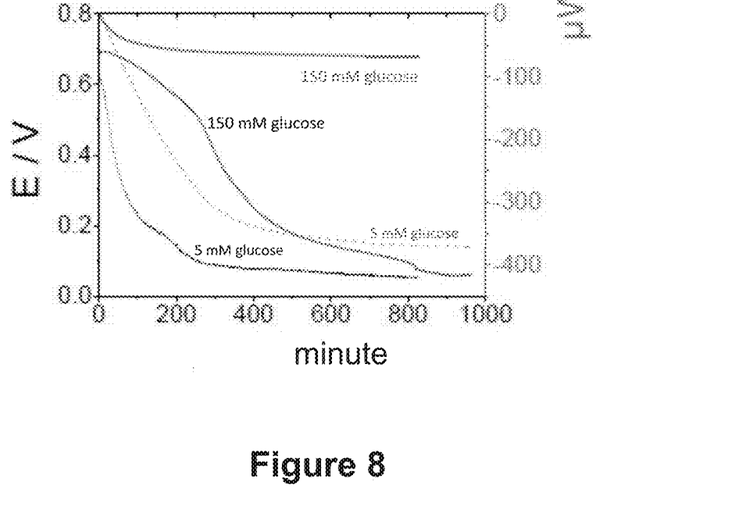
FIG. 8 shows the energy production by continuous discharge at 6 kΩ in µW·h versus time (minutes) and total glucose consumption for pads soaked in glucose at 5 mM and 150 mM for the biocell of Example 3.
Figure 9:
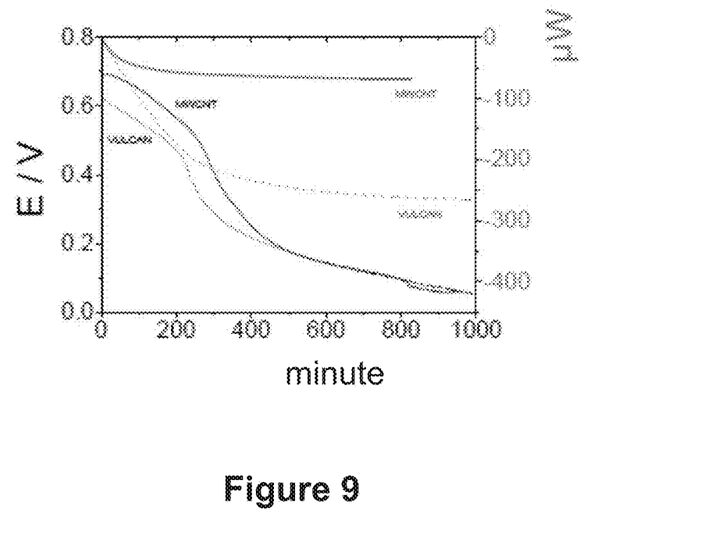
FIG. 9 shows the energy production by continuous discharge at 6 kΩ in µWh versus time (minutes) and total glucose consumption for pads soaked in 150 mM glucose for the biocell of Example 3 (carbon black) and that of Example 1 FAB-GDH/BOD on MWCNTs.

FIG. 8 shows the energy production by continuous discharge at 6 kΩ in μW·h versus time (minutes) and total glucose consumption for pads soaked in glucose at 5 mM and 150 mM for the biocell of Example 3 (carbon black). FIG. 9 shows the energy production by continuous discharge at 6 kΩ in μWh versus time (minutes) and total glucose consumption for pads soaked in 150 mM glucose for the biocell of Example 3 (carbon black) and that of Example 1 FAD-GDH/BOD on MWCNTs.

The best performances are obtained for the cell based on MWCNTs which makes it possible to generate 400 µWh after a continuous discharge which consumes all of the 150 mM of available glucose.

Example 4: Single-Reservoir Biocell

Figure 10:
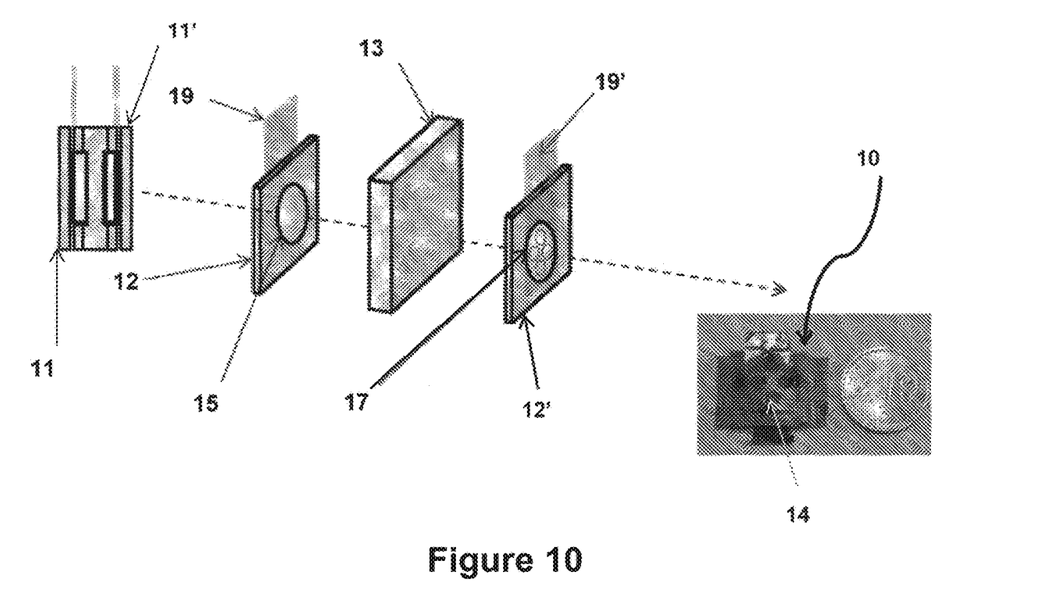
FIG. 10 includes a partial exploded diagram of the structure of a biocell 10 shown in Example 4 as well as a front view thereof, and on the left a sectional view.

FIG. 10 comprises a diagram of the structure of a biocell 10 according to this particular example.

For the biocathode, 8.75 mg of MWCNT functionalized with protoporphyrin IX as described in Example 1 were ground in the presence of 3.75 mg of BOD and 25 µl of distilled water. For the bioanode, 8.75 mg of MWCNT, 3.75 mg of GOx, 2.5 mg of catalase from bovine liver and 1.25 mg of 1,4-naphthoquinone were ground with 25 µL of distilled water.

Each pellet 15 and 17 is formed in situ on a frame which comprises a PTFE sheet 12 or 12' having a thickness of 0.25 mm and pierced with a circular hole of 1 cm in diameter. This template is placed on a support consisting of an adhesive sheet of fiberglass and PTFE 11 or 11' of thickness 70 µm. A GEL tab 19 or 19' is positioned vis-à-vis the circular hole of the PTFE sheet 12 or 12' between the circular hole and the adhesive sheet 11 or 11'. This sheet 11 and 11' is not shown in the exploded view. A sufficient quantity of each homogeneous paste of bioanode or biocathode (an amount of about 12 mg per pellet makes it possible to fill a template) is positioned in the hole and is compressed directly on the support by a press. This makes it possible to obtain pellets of 1 cm in diameter and 0.25 mm in thickness. These pellets on a support formed in situ can then be used as bioanodes and biocathodes.

The adhesive sheet 11' of the biocathode is pierced with 4 holes 14 of 2 mm in diameter to allow the diffusion of oxygen from the air to the biocathode. Although the adhesive covering sheet 11 or 11' is not shown in the exploded view of FIG. 10, the positions which the holes would take are indicated therein. The dimensions of the PTFE sheet serving as the 12 or 12' frame is approximately 20 mm×20 mm. The outer support sheets 11 and 11' which serve as protection are of larger dimensions and allow, by contact of their facing adhesive surfaces, to secure or join the elements of the device. Their adhesive faces being face to face, they can be joined to one another and secure the biocell on some of its sides. An example of this variant is the subject of a photograph framed in FIG. 10. The flexible outer sheet 11' pierced with holes 14 and extending laterally from right and left to cover and adhere to the symmetrical parts of the sheet 11 which overlap each other, can be seen. A 10 euro cent coin allows one to visualize the size of the biocell obtained.

A thick blotting sheet 13 (as used in the preceding examples) substantially of the same size as the PTFE sheet serving as a frame is then placed between the bioanode 15 and the biocathode 17. The GDL tabs 19 and 19' serve as both a current collector and a support for the pads 15 or 17.

A GDL tab 19 is therefore positioned facing the anode pad 15, and a GDL tab 19' is also positioned facing the cathode pad 17. These two tabs 19 and 19' project from their respective support 12 and 12'. They are positioned between the PTFE frame 12 or 12' and the outer support sheet 11 or 11'. These tabs 19 and 19' serve both as a current collector and as a support for the pad which is associated with them and makes it possible to connect the device to an electrical receiver. In the front view of the biofuel cell 10, tabs 19 and 19' protrude from opposite sides of the device according to the invention, while in the exploded view these tabs 19 and 19' are shown projecting from the same side. Both arrangements are possible.

Whatever the final particular shape of a biocell according to the invention, it comprises a passage allowing access of the glucose-based fuel to the pad 13. Here the glucose solution is added by injecting a glucose solution using a syringe.

Figure 12:
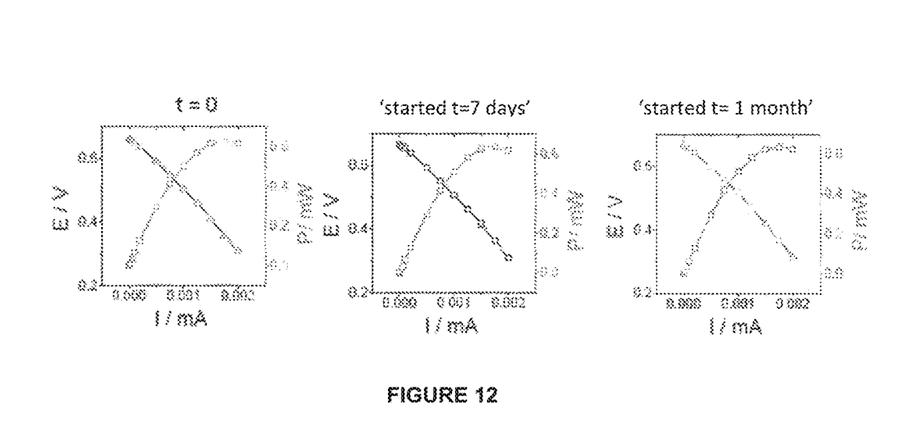
FIG. 12 represents the polarization and power curves of the biocell according to Example 4 at t=0, t=7 days and t=1 month for a 150 mM glucose solution.
Figure 13:
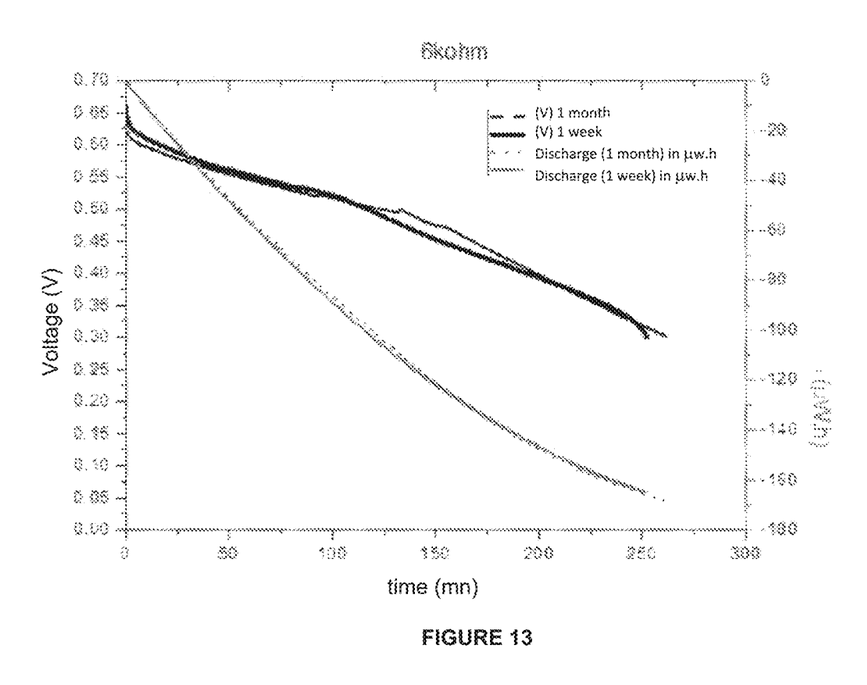
FIG. 13 shows the energy production by continuous discharge at 6 kΩ in µWh versus time (minutes) and total glucose consumption for a 150 mM glucose solution for the biocell of Example 4.

FIG. 12 shows that the biocell retains its performance whether it is measured after a week or 1 month. FIG. 13 confirms that by testing the discharge of the biocell, it also retains 100% of its performance whether it is started after a week or a month. This validates the capacity of the biocell to power a device at least 1 month after its manufacture without loss of performance.

Example 5 Serial Pellet Biocells

Figure 11:
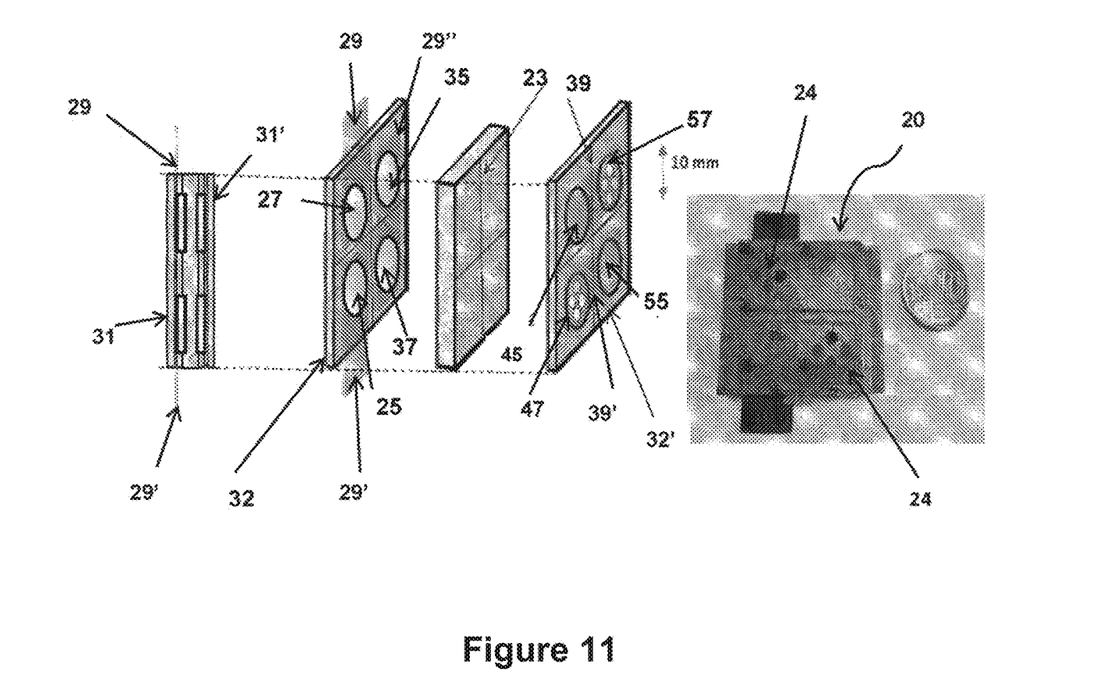
FIG. 11 includes a partial exploded diagram of the structure of a biocell 20 shown in Example 5 as well as a front view thereof, and on the left, a sectional view.

FIG. 11 comprises a diagram of the structure of a biocell 20 according to this particular example.

The anode and cathode pellets used are of the same type as those used for the device of Example 4.

Four pellets, two anode 25 and 35, and two cathode 27 and 37 are placed on the adhesive surface of a first adhesive sheet of fiberglass and PTFE 31 and in four circular openings of a frame of PTFE 32 of dimensions 35 mm×35 mm. These sheets are of identical materials and thicknesses to those described in Example 4. The four pads are positioned in a quadrilateral pattern and each anode pad 25 and 35 is arranged diagonally to each other as are the cathode pads 27 and 37.

Another set of four pellets in a frame of PTFE 32' are arranged on a second sheet of fiber and PTFE 31'. On the second frame 32', the 4 pellets are alternated in a symmetrical arrangement: two anode pellets 45 and 55, and two cathode cells 47 and 57 each diagonally to the other.

The electrochemical cells are set up serially by the use of GDL tabs 29, 29', and 29" positioned between the adhesive outer sheet 31 and the PTFE frame 32 and tabs 39 and 39' positioned between the outer sheet 31' adhesive and 32' PTFE frames. It should be noted that in the exploded diagram of FIG. 11 the position of the tabs on the PTFE frame 32 is seen by transparency: the tabs are in fact positioned behind the face of the frame shown. This is done in order to be able to appreciate the respective positioning of the tabs. Their relative position is better explained in the associated section view. On the PTFE frame 32', the tab 39 positioned horizontally between the pellets 45 and 57 makes it possible to connect the electrochemical cell consisting of the anode 45 and the cathode 27 to that consisting of the anode 35 and the cathode 57. Likewise, the tab 29" positioned vertically between the pellets 35 and 37 makes it possible to connect the cell consisting of the anode 35 and the cathode 57 to that consisting of the anode 55 and the cathode 37. The tab 39' positioned horizontally between the pellets 55 and 47 makes it possible to connect the cell consisting of the anode 55 and the cathode 37 to that consisting of the anode 25 and the cathode 47. The tongues 29 and 29', respectively in contact with the cathode 27 and the anode 25 project outside the circuit in opposite directions and allow the device to be connected to an electrical receiver (not shown).

As in example 4, the pellets are formed by compression in situ by adding a quantity of paste in the circular holes of 10 mm in diameter preformed in the frame 32 or 32'. The tabs 29, 29', 29", 39 and 39' are positioned beforehand between the sheet of fiberglass and PTFE 31 and 31' serving as a support and the PTFE frame 32 and 32'.

A set of 4 holes 24 of 2 mm in diameter are made on the fiberglass and PTFE support sheets 31 and 31' at the back of each of the 4 biocathodes 27, 37, 47 and 57 (and the portion of corresponding GDL tabs) and allow the diffusion of oxygen from the air to the biocathode. The position of these series of openings 24 is also indicated on the partial exploded view of the device 20 although the openings are made in the sheets 31 and 31', not shown in the partial exploded view.

A reservoir, or pad, 3 mm thick and of substantially the same size, or slightly smaller, than that of the PTFE frames 32 and 32' is interposed between the two sheets carrying the PTFE frames 31 and 31', the pellets 27, 35, 37, 25 and 45, 57, 55, 47, and carrying the tabs 29, 29' and 29". This pad 23 is directly in contact with one side of the pads 27, 35, 37, 25, 45, 57, 55 and 47. This pad is made of thick blotter of the same type as that described previously in example 4.

The outer covering sheets 31 and 31' which serve as protection and support are of larger dimensions than the PTFE frame and therefore project beyond these frames 32 and 32'. Thus, these sheets 31 and 31' make it possible, by contact with their opposite adhesive surfaces, to secure, or join, the elements of the device. Their adhesive faces being opposite, they can be joined to one another and secure the biocell on some of its sides. An example of this variant is the subject of the front view of FIG. 20. We can see the flexible outer sheet 31' pierced with a series of holes 14, the edges of which extend laterally to the right and to the left to cover and adhere to the symmetrical pails of the sheet 31 by overlapping each other.

The frames 32 and 32' are placed face to face so that each anode patch 25, 35 placed on a first sheet 32 is opposite a cathode patch 47 and 57 placed on the other PTFE sheet 32. Likewise, each anode patch 27, 37 placed on the first PTFE sheet 32 is opposite a cathode patch 45 and 55 placed on the other PTFE sheet 32'. The reservoir 23, made of a thick blotting sheet of the same size as the PTFE sheets 32 and 32', is then placed between them. The device 30 is then obtained by contacting the outer covering sheets 31 and 31' with one another.

Example 6: Comparison of the Serial Pellet Biocells of the Previous Example with a Single Pellet A biocell 40 according to the invention was produced to compare the efficiency of the serial devices described in example 5 with a biocell of the same type but comprising only a pair of pellets, and not 4, mounted serially, amounts of materials being equal. A biocell comprising a pair of circular bio-anodic and bio-cathodic pellets, identical to Example 5 in all points, except for their diameters, was produced. The diameter of the pellets is 20 mm.

Figure 14:
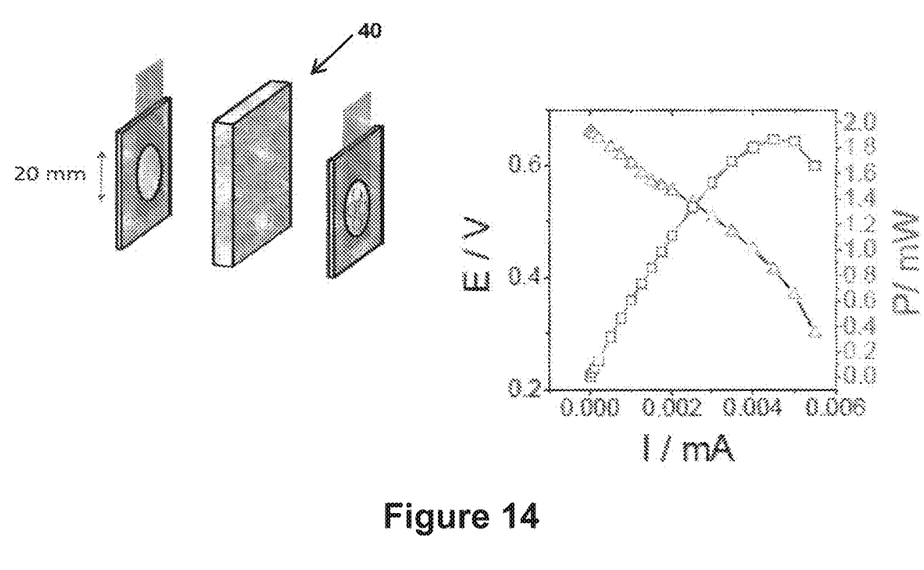
FIG. 14 represents the polarization and power curves of the biocell described in Example 5 and in FIG. 11 for a 150 mM glucose solution.
Figure 15:
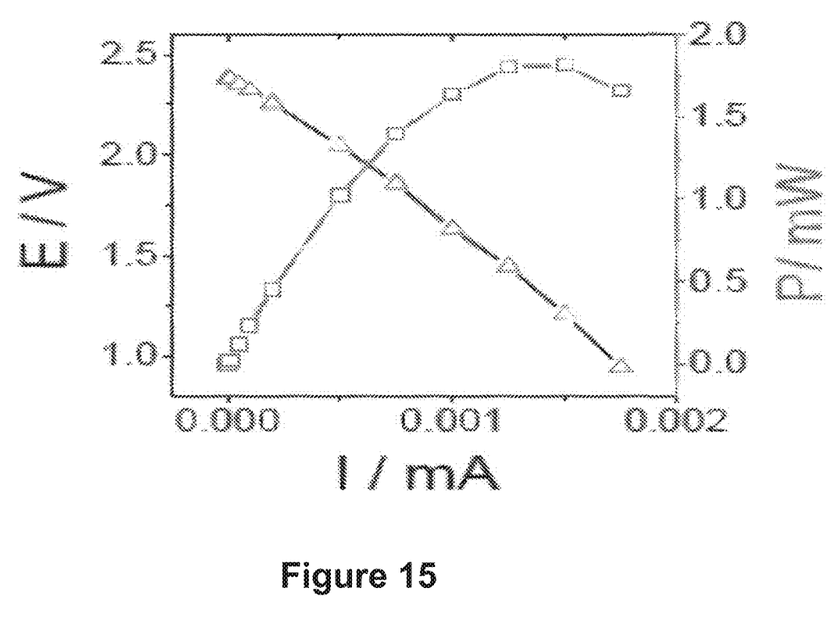
FIG. 15 represents the polarization and power curves of the biocell described in Example 6 for a 150 mM glucose solution.

FIG. 14 shows the polarization and power curves of the 20 mm pellet biocell. The figure shows that if we increase the size of the pellets by two, we obtain a power multiplied by approximately two. FIG. 15 shows the polarization and power curves of the biocell described in example 5. It shows that if two biofuel cells are placed serially in the same device, the emf and the battery power are increased by two.

The invention claimed is:

1. A biocell with a biofuel reservoir, the biocell being intended to be brought into contact with a liquid medium, the liquid medium and with a fluid medium comprising an oxidizer, the biocell comprising a first electrochemical cell, the first electrochemical cell comprising:
   an anode made of a solid agglomerate comprising a conductive material mixed with a first enzyme capable of catalyzing the oxidation of the biofuel;
   a cathode made of a solid agglomerate comprising a conductive material mixed with a second enzyme capable of catalyzing the reduction of the oxidant, and
   a separating and porous membrane, electrically insulating, and permeable to the liquid medium, placed between the anode and the cathode,
   the biocell further comprising means for electrically switching on of the biofuel with an electric receiver, the means for switching in an electrical circuit allowing a current to flow from the cathode to the anode;
   the biocell comprises a means for storing the biofuel and for providing the liquid medium to the anode, the means comprising a hydrophilic porous material in contact with the anode and having a surface mass of 500 to 900 $g/m^2$.

2. The biocell according to claim 1, wherein the biofuel storage means has a thickness of 1 cm to 0.1 mm.

3. The biocell according to claim 1, wherein the hydrophilic porous material is cellulose-based.

4. The biocell according to claim 1, wherein the means for storing biofuel and providing liquid is also the separating and porous membrane.

5. The biocell according to claim 1, wherein the means for switching on the device comprise a tab of pyrolytic graphite.

6. The biocell according to claim 1, wherein the anode is in the form of a pellet.

7. The biocell according to claim 1, wherein the anode is held in a frame, the frame being either the means for storing the biofuel and providing the liquid medium, or an electrically insulating material such as PTFE.

8. The biocell according to claim 1, the biocell comprising an outer covering, which comprises openings positioned and dimensioned so as to allow access to a liquid at the anode and/or gas at the cathode.

9. The biocell according to claim 8, the outer covering preferably flexible and insulating.

10. The biocell according to claim 1, wherein the liquid medium is an aqueous liquid medium.

11. The biocell according to claim 10, wherein the aqueous liquid comprises a biofuel.

12. The biocell according to claim 1, wherein the liquid medium comprises a biofuel.

* * * * *